United States Patent [19]

Kuroda et al.

[11] Patent Number: 5,769,971
[45] Date of Patent: Jun. 23, 1998

[54] MANGANESE-ALUMINUM MAGNET WITH FAR-INFRARED RADIATION EFFECT AND METHOD OF MANUFACTURING THE SAME

[75] Inventors: Naoto Kuroda; Atsushi Ohkawa; Noriyuki Umano, all of Himeji; Yutaro Iso, Tokyo, all of Japan

[73] Assignee: Creation Renai Co. Ltd., Tokyo, Japan

[21] Appl. No.: 694,371

[22] Filed: Aug. 8, 1996

[30] Foreign Application Priority Data

Aug. 10, 1995 [JP] Japan ................................. 7-227445

[51] Int. Cl.[6] ................................................. C22L 22/00
[52] U.S. Cl. ........................................ 420/434; 252/62.55
[58] Field of Search .................................. 148/314, 424; 420/434; 252/62.55

[56] References Cited

U.S. PATENT DOCUMENTS 5,138,133   8/1992   Sakurada et al. ....................... 219/211

Primary Examiner—John Sheehan
Attorney, Agent, or Firm—Armstrong, Westerman, Hattori, McLeland & Naughton

[57] ABSTRACT

A magnet having high mechanical strength, and resistance to corrosion, which may be machined and polished to a metallic gloss is made by mixing, molding and hot extruding of a manganese-aluminum raw material, which may contain Mn, C, Ni and Al, and a powder of a far-infrared radiation material such as tourmaline, black lead, and zirconium silicate.

5 Claims, No Drawings

MANGANESE-ALUMINUM MAGNET WITH FAR-INFRARED RADIATION EFFECT AND METHOD OF MANUFACTURING THE SAME

BACKGROUND OF THE INVENTION

1. Field of the Invention

The present invention generally relates a magnet, and particularly to a magnet composed of a composite material of a magnet material and a material having an effect of far-infrared radiation and a method of manufacturing the same.

2. Description of the Prior Art

It is known that magnetism has an effect to improve the circulation of the blood in a human body and an effect to activate surroundings of animals and plants, soil and water, and so on, and it is also known that far-infrared rays have an effect to improve the circulation of the blood and an effect to improve the metabolism. Health and medical appliances utilizing these effects have been practically used. Further, as a composite material from which such effects can be obtained at the same time, that in which an Nd-Fe-B magnet material and a far-infrared radiation material are combined through a binder such as resin, rubber or the like, is known, for example, by Japanese Patent Unexamined Publication No. Hei-5-347206.

In this method, however, since molding is carried out with a binder such as resin, rubber or the like, it is difficult to perform machining on the molded material, and even if the molded material is polished, it is difficult to make the molded material have metallic gloss. Accordingly, this method has a disadvantage that it is difficult to use this method in producing articles to be used also as accessories. Further, in accordance with uses, the mechanical strength is not always satisfactory.

It is therefore an object of the present invention to solve the problems in the prior art.

It is a further object of the present invention to provide a method of manufacturing a metal magnet with a far-infrared radiation effect, which can be subjected to machining, which has high mechanical strength, which is hardly damaged, and which can be made to have metallic gloss by polishing.

SUMMARY OF THE INVENTION

In order to achieve the above objects, according to an aspect of the present invention, provided is a method of manufacturing a manganese-aluminum magnet with far-infrared radiation effect comprising the steps of: mixing powder of manganese-aluminum magnet raw material with powder of far-infrared radiation material; molding the mixture powder; and hot-extruding the molding to thereby obtain the manganese-aluminum magnet with far-infrared radiation effect.

Preferably, the above method further comprises a step of atomizing a molten alloy consisting of Mn, C, Ni and Al under presence of Ar to thereby prepare the powder of manganese-aluminum magnet raw material.

Preferably, in the above method, the mixing rate of the powder of far-infrared radiation material is selected to be 5–30 weight % relative to the powder of manganese-aluminum magnet raw material.

Preferably, in the above method, the powder of far-infrared radiation material is ceramics powder selected from tourmaline, black lead, and zirconium silicate.

Preferably, in the above method, the contents in weight % of Mn, C, Ni and Al are 68.8%, 0.44%, 0.78% and the residue, respectively.

According to another aspect of the present invention, provided is a method of manufacturing a manganese-aluminum magnet with far- infrared radiation effect comprising the steps of: mixing powder of manganese-aluminum magnet raw material with powder of far-infrared radiation material to thereby obtain a mixture powder; filling a cylindrical capsule made from a mild steel plate with the mixture powder and sealing said capsule; hot-extruding the said capsule filled with the mixture powder; and removing said capsule to thereby obtain the manganese-aluminum magnet with far-infrared radiation effect.

According to a further aspect of the present invention, a manganese-aluminum magnet with far-infrared radiation effect obtained through mixing, molding and hot-extruding of powder of manganese-aluminum magnet raw material and powder of far-infrared radiation material.

Preferably, in the above manganese-aluminum magnet with far-infrared radiation effect, the mixing rate of the powder of far-infrared radiation material is selected to be 5–30 weight % relative to the powder of manganese-aluminum magnet raw material.

Preferably, in the above manganese-aluminum magnet with far-infrared radiation effect, the powder of far-infrared radiation material is ceramics powder selected from tourmaline, black lead, and zirconium silicate.

Preferably, in the above manganese-aluminum magnet with far-infrared radiation effect, the powder of manganese-aluminum magnet raw material contains Mn, C, Ni and Al.

Preferably, in the above manganese-aluminum magnet with far-infrared radiation effect, the contents in weight % of Mn, C, Ni and Al are 68.8%, 0.44%, 0.78% and the residue, respectively.

Being a metal magnet using no binder, the manganese-aluminum magnet having an effect of far-infrared radiation according to the present invention has high mechanical strength. Accordingly, the material according to the present invention is hardly damaged. Further, it is possible to make the material have a desired shape by machining and it is possible to make it have metallic gloss by polishing.

If this magnet is used in a state that the magnet is machined circularly and the circular magnet is sewn in a cushion, a mattress, or the like, it is possible to obtain an excellent effect to improve health by the synergistic effect of the high magnetic and far-infrared radiation effects of the magnet. Further, if this magnet is machined and polished into various shapes such as a spherical shape etc., this magnet can be used for a bracelet, a necklace, and so on, having not only a health improvement effect but also a function as an ornament.

Further, in the case of using this magnet for improvement of soil or water quality, the effect of the magnet lasts for a long time because the manganese-aluminum magnet has corrosion resistance.

As the material for far-infrared radiation according to the present invention, crushed powder of a ceramics material such as tourmaline, black lead, zirconium silicate, or the like, may be used.

DESCRIPTION OF THE PREFERRED EMBODIMENTS

Molten alloy containing Mn by 68.8 weight %, C by 0.44 weight %, Ni by 0.78 weight % and Al as balance was atomized with an Ar gas to thereby prepare spherical powder having an average grain size of 46 $\mu$m. This powder was mixed with powder, having average grain size of 5 $\mu$m, of tourmaline having a far-infrared radiation characteristic by means of a V-type mixer.

Next, the mixture powder was poured into a cylindrical capsule made from a mild steel plate and having a diameter of 58 mm and height of 87 mm so that the capsule was filled with the mixture powder. The capsule was heated to 720° C. after sealed, and then subjected to die extrusion twice so as to be made into a round bar having a diameter of 16.3 mm. The round bar was cooled and the outer circumferential capsule material was removed by grinding to thereby obtain a round bar molding having a diameter of 15 mm. The round bar molding was cut into 4 mm-thick pieces by means of a precision type thin-blade rotary abrasive wheel to thereby obtain steel samples for various tests.

TABLE 1

| No. | | Mixture rate of ceramics powder (weight %) | Magnetic characteristic (BH) max (MGOe) | Far-infrared radiation effect | Machinability |
|---|---|---|---|---|---|
| 1 | Comparative | 0 | 5.5 | None | Excellent |
| 2 | Comparative | 2 | 5.4 | None | Excellent |
| 3 | Embodiment | 5 | 3.9 | Yes | Excellent |
| 4 | Embodiment | 10 | 3.7 | Yes | Excellent |
| 5 | Embodiment | 15 | 3.2 | Yes | Good |
| 6 | Embodiment | 20 | 3.0 | Yes | Good |
| 7 | Embodiment | 25 | 2.7 | Yes | Fairly good |
| 8 | Embodiment | 30 | 2.3 | Yes | Fairly good |
| 9 | Comparative | 35 | 1.8 | Yes | Fail |

The mixture rate of the ceramics powder to the Mn—Al—C alloy powder, the magnetic characteristic, the far-infrared radiation characteristic, and the machinability of the extruded material obtained by such a producing method as described above are shown in Table 1.

Although the more the mixture rate of the ceramics powder increased, the more the magnetic characteristic decreased, sufficient magnetic characteristic as a magnet for health could be obtained even in the case of the 30% mixture rate, as the result. Further, as for the far-infrared radiation characteristic, radiation was confirmed even in the case of the 5% mixture rate. On the other hand, if the mixture rate is increased to 35% content, the machinability is lowered. Accordingly, it is preferably to select the mixture rate of the ceramics powder to the manganese-aluminum magnet raw-material powder to be in a range of from 5 to 30 weight %.

Being obtained through mixing, molding and hot-extrusion of powder of manganese-aluminum magnet raw material and powder of far-infrared radiation material, the manganese-aluminum magnet having an effect of far-infrared radiation according to the present invention is able to be subjected to machining, is able to be made to have metallic gloss by polishing, is high in mechanical strength, is hardly damaged, is superior in corrosion resistance, and is superior in magnetic characteristic as well as far-infrared radiation characteristic. Accordingly, the manganese-aluminum magnet having an effect of far-infrared radiation according to the present invention has superior effects that it can be used, for a long term, for health and medical instruments, and for improvement of soil as well as water quality.

What is claimed is:

1. A manganese-aluminum magnet obtained through mixing, molding and hot-extruding of powder of a manganese-aluminum magnet raw material and powder of a far-infrared radiation material.

2. A manganese-aluminum magnet according to claim 1, wherein the mixing rate of the powder of far-infrared radiation material is 5–30 weight % relative to the powder of manganese-aluminum raw material.

3. A manganese-aluminum magnet according to claim 1 or 2, wherein the powder of far-infrared radiation material is a ceramics powder selected from the group consisting of tourmaline, black lead, and zirconium silicate.

4. A manganese-aluminum magnet according to claim 1 or 2, wherein the powder of manganese-aluminum magnet raw material contains Mn, C, Ni and Al.

5. A manganese-aluminum magnet according to claim 4, wherein the contents in weight % of Mn, C, Ni and Al are 68.8%, 0.44%, 0.78% and the balance respectively.

* * * * *